United States Patent
Kole et al.

(10) Patent No.: US 7,416,787 B2
(45) Date of Patent: Aug. 26, 2008

(54) MEDICAL EQUIPMENT PROVIDED WITH A COATING

(75) Inventors: Henk Kole, Eindhoven (NL); Anna Louise Bouwkampwijnoltz, Eindhoven (NL); Petrus Egidius Jacobus Legierse, Eindhoven (NL); Cornelis Gerardus Visser, Eindhoven (NL); Marcel Rene Boehmer, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 58 days.

(21) Appl. No.: 10/551,072

(22) PCT Filed: Mar. 26, 2004

(86) PCT No.: PCT/IB2004/050348

§ 371 (c)(1),
(2), (4) Date: Sep. 27, 2005

(87) PCT Pub. No.: WO2004/087031

PCT Pub. Date: Oct. 14, 2004

(65) Prior Publication Data

US 2006/0177672 A1   Aug. 10, 2006

(30) Foreign Application Priority Data

Mar. 31, 2003   (EP) .................... 03100836

(51) Int. Cl.
B32B 9/04   (2006.01)

(52) U.S. Cl. ............. 428/447; 427/387; 106/287.14; 106/287.15

(58) Field of Classification Search ............. 428/447; 106/287.14, 287.15; 427/387
See application file for complete search history.

(56) References Cited

U.S. PATENT DOCUMENTS

| | | | | |
|---|---|---|---|---|
| 4,027,073 A * | 5/1977 | Clark | | 428/412 |
| 5,736,251 A * | 4/1998 | Pinchuk | | 428/447 |
| 6,001,163 A * | 12/1999 | Havey et al. | | 106/287.13 |
| 6,291,070 B1 | 9/2001 | Arpac et al. | | |
| 6,596,402 B2 * | 7/2003 | Soerens et al. | | 428/447 |
| 7,160,592 B2 * | 1/2007 | Rypacek et al. | | 428/36.9 |
| 2001/0032568 A1 | 10/2001 | Schutt | | |
| 2003/0157344 A1* | 8/2003 | Shoup et al. | | 428/447 |
| 2004/0029834 A1* | 2/2004 | Schiestel et al. | | 514/63 |
| 2005/0008763 A1* | 1/2005 | Schachter | | 427/2.24 |

FOREIGN PATENT DOCUMENTS

| | | |
|---|---|---|
| EP | 0 501 055 A1 | 9/1992 |
| JP | 01-185262 | 7/1989 |
| JP | 01-259845 | 10/1989 |
| WO | WO 98/13434 A1 | 4/1998 |
| WO | WO 02/36701 A1 | 5/2002 |

OTHER PUBLICATIONS

Novak, B.A.; Hybrid Nanocomposite Materials-Between Inorganic Glasses and Organic Polymers; 1993; Adv. Mater.; 5:(6)422-433.
Schmidt, H.; New Type of Non-Crystalline Solids Between Inorganic and Organic Materials; 1985; J. Non-Cryst. Solids; 73:681-691.
Schmidt, H., et al.; Organically Modified Ceramics and Their Applications; 1990; J. of Non-Cryst. Solids; 121:428-435.

* cited by examiner

Primary Examiner—Margaret G Moore
(74) Attorney, Agent, or Firm—Yan Glickberg

(57) ABSTRACT

Disclosed is medical equipment, the surface of which being at least partially provided with a coating which is provided by means of a sol-gel process. By applying such coating staining of the medical equipment by iodine-containing agents is prevented. The sol-gel coating can be cured at a curing temperature of 80° C. or lower. The medical equipment can, for example, comprise a tabletop of a diagnostic system.

7 Claims, No Drawings

MEDICAL EQUIPMENT PROVIDED WITH A COATING

The invention relates to medical equipment that is at least provided with a coating.

Medical equipment, such as for example a tabletop of a diagnostic system, is frequently exposed to chemical compounds such as iodine-containing agents. Said compounds often cause staining of the surface of the equipment, thereby deteriorating the appearance thereof.

In Japanese patent application JP 01-259845 a coated tabletop of a medical table for accommodating a patient has been described. The tabletop is coated with a urethane film to generate no X-ray transmission characteristics and virtual image, to suppress slip, and to hold beautiful appearance. It is further described that the film has good releasability to almost all of the chemicals used in medical treatment. However, it was found that the resistance against iodine-containing agents is poor. It was found that spilled iodine, for instance from iodine-containing contrast solutions, penetrates the urethane film, giving iodine stains that cannot be removed. The appearance of the film thereby strongly decreases. It is an object of the invention to provide medical equipment that is much more resistant against, for example, iodine stains, and nevertheless maintains the above other advantageous properties.

To this end, the present invention provides for medical equipment, the surface of which being at least partially provided with a coating which is provided by means of a sol-gel process.

It is noted that sol-gel coatings (or lacquers) per se are known in the art. In PCT patent application WO 98/13434 products for personal care, particularly electric shavers, are provided with a coating that contain a network of a hydrolytically condensed organosilane compound. This coating is provided to the shaver to protect it against compositions for personal care, such as cosmetics, lotions, shampoos and other skin-care products, particularly shaving lotions, such as pre-shaves and aftershaves, which are found to be aggressive relative to other coatings. However, the advantageous properties of such coatings for use in medical equipment for preventing iodine staining are not disclosed.

Advantageously, the sol-gel process at least comprises the step of mixing together an organosilane compound and water.

Preferably, the sol-gel process at least comprises the step of mixing together an organosilane compound and silica particles.

The coating materials according to the present invention are known as materials obtained by means of a sol-gel process or, if they are combined by means of organic polymers, as hybrid or composite materials, heteropolysiloxanes, ormocers, or ormosils. However, these materials are not understood to be siloxanes formed from linear chains or silicone rubbers derived from said siloxanes or other inorganic polymers having a low cross-link density. Preferably, the coating is made of a hydrolytically condensed organosilane sol-gel composition. An organosilane compound or a substituent contained therein is considered to be hydrolytically condensable when the compound contains a silanol group, —Si—OH, or when a silanol group can be formed from said compound by using water, and two silanol groups can react to form an Si—O—Si bond while eliminating water. When these reactions have (partially) taken place, then the compound is (partially) hydrolytically condensed. If the organosilane compound comprises three or more hydrolytically condensable substituents, a network can be formed by hydrolytic condensation. If the above-mentioned substituents are linked to one silicon atom, then said silicon atom serves as the cross-link. This and other information on sol-gels is known in the art, for example from B. M. Novak in Adv. Mat., 5(6), 1993, p. 422, or H. Schmidt in J. Non-Cryst. Sol. 73, 1985, p. 681, and J. Non-Cryst. Sol. 121, 1990, p. 428.

Suitable hydrolytically condensable organosilane compounds are compounds in accordance with the formula $SiX_pY_qZ_r$, wherein X is a hydrolytically condensable substituent selected, for example, from the group formed by halogen, hydroxy, alkoxy, acyloxy or amino, Y is a polymerizable substituent R-A, wherein R is an alkylene or arylalkylene, possibly interrupted by an oxygen atom or a sulfur atom, or an NH-group, and the substituent A is selected, for example, from the group formed by halogen, amino, amide, aldehyde, alkylcarbonyl, carboxy, thio, cyano, alkoxy, alkloxycarbonyl, sulfonic acid, phosphoric acid, acryloxy, methacryloxy, epoxy or vinyl, and Z is a hydrolytically non-condensable and non-polymerizable substituent which is selected, for example, from the group formed by alkyl and aryl, wherein p is equal to 2, 3, or 4, q is equal to 0, 1, or 2, r is equal to 0 or 1, p+q is greater than 2 and p+q+r is equal to 4. Each time X, Y, or Z occurs, it is possible, of course, to make a new choice from the above-mentioned groups. Coatings are preferably prepared from mixtures of the above-mentioned organosilane compounds.

In a suitable method of processing said organosilane compounds, an approximately stoichiometric quantity of water is added, so that the hydrolytically condensable substituents are hydrolyzed, thereby forming —Si—OH groups, which while eliminating water, condense to form Si—O—Si bonds. If necessary, said processing step can be carried out in a solvent, and, preferably, an acid, such as hydrochloric acid, or a base, such as caustic soda, is used as a catalyst. Polymerization of the polymerizable substituents by means of radical-polymerization or condensation-polymerization takes place in ways known to those skilled in the art.

A coating can be obtained, for example, by partly hydrolytically condensing an organosilane compound at room temperature, thereby forming a sol, which sol is subsequently provided on a substrate by means of, for example spin-coating, after which the hydrolytic condensation is completed by curing the coating at an elevated temperature, thereby forming the network.

In a preferred embodiment, the organosilane compound comprises tetraethoxysilane (TEOS).

Coatings which are prepared from organosilane compounds containing four hydrolytically condensable substituents, such as tetraethyl orthosilicate, exhibit a good resistance to iodine-containing compositions. In order to obtain a high cross-link density, without the coating exhibiting cracks, glycidoxypropyl trimethoxysilane (GLYMO) is preferably also used as an organosilane compound.

In order to further avoid the development of cracks, particularly if the coatings are thicker than approximately 500 nm, the organosilane compound preferably comprises methyltromethoxysilane (MTMS).

In a preferred coating material at least one substituent of the organosilane compound is not hydrolytically condensable. In terms of the formula $SiX_pY_qZ_r$, this means that p is chosen to be in the range of 2.0 to 4.0. Because of the resistance to emollients, p is preferably in the range of 3.0 to 3.5. Suitable organosilane compounds are, for example, alkyl trialkoxysilanes, such as methyl trimethoxysilane, methyl triethoxysilane, ethyl trimethoxysilane, ethyl triethoxysilane, tetraethoxysilane. Phenyl trimethoxysilane and epoxy-silane derivatives such as glycidoxypropyl trimethoxysilane are suitable too. These organosilane compounds can be used alone or in mixtures to form coatings having a thickness of at least 10 micrometers, and, if desirable, dyes, pigments or other fillers, such as silica particles, dispersions, or soot, may be added to said coatings.

It is preferred that the organosilane compound contains an organic, polymerizable substituent. The use of an organic, polymerizable substituent enables a high cross-link density to be achieved, without the coating exhibiting cracks, so that a very good resistance to emollients is achieved. In terms of the formula $SiX_pY_qZ_r$, in this case, q is equal to 1 or 2. Preferably, q is equal to 1. Suitable organosilane compounds are epoxides, such as 3-glycidoxypropyl trimethoxysilane (GLYMO), by means of which a polyether chain between silicon atoms can be realized, (meth)acrylates, such as methacryloxypropyl trimethoxysilane, or vinylsilanes, such as vinyl trimethoxysilane.

The coating may also contain inorganic or organic pigments, photocatalytic pigments and dyes in all available colors, including coated and non-coated aluminum pigments and (optical) interference and view-angle dependant multicolor pigments.

The coatings may be glossy or may have a matt appearance. If a matted coating is preferred, a matting agent as known in the art may be added to the composition.

Preferably, the coating has been cured at a curing temperature of 80° C. or lower.

It is preferred to use sol-gels that can be cured at a curing temperature of 80° C. or lower, particularly when applied on tabletops of medical equipment. It is noted that the coatings of the prior art have curing temperatures of 130° C. or higher, which supersede the maximum temperature impact of 80° C. for such tabletops, above which a loss of mechanical (loading) strength is observed. The sol-gel compositions according to this invention have a curing temperature of 80° C. or lower. It is stressed that UV curable sol-gel compositions are encompassed in this definition, as long as the UV curing is performed at 80° C. or lower. It will, however, be clear to the skilled person that while the sol-gels according to the present invention can be cured at 80° C., curing at higher temperatures, if required, can also take place.

Sol-gels that can be cured at about or below 80° C. and that do not affect in a negative way the mechanical strength of substrates like tabletops of medical and diagnostic systems, may, for instance, be made of mixtures of tetraethoxysilane, glycidoxypropyl trimethoxysilane, and silica dispersion. These coatings proved to be resistant to a solution of 1 wt. % iodine in 70 wt. % ethanol for at least 3 hours. It goes further without saying that the coating should satisfy the other normal requirements for medical equipment, such as biocompatibility, resistance against X-radiation, disinfectants, and cleaning agents, and the like.

In a preferred embodiment of the invention an acid is added during the sol-gel process for making the coating, which acid is chosen from the group comprising malonic acid, dimethylmalonic acid and itaconic acid.

By adding an acid from the above group during the sol-gel process a crack and stain free sol-gel layer can be obtained.

The invention in particular relates to medical equipment, which is at least partially provided with a coating of said sol-gel composition, i.e. at parts that can come in contact with iodine-containing agents. The invention is particularly useful for tabletops of diagnostic systems that can come easily in contact with iodine-containing solutions, such as contrast solutions, medical cleaning solutions, disinfectants, and the like.

It was found that sol-gel hybrid coatings, as described hereinbefore, have further high mechanical, chemical, and heat resistance.

The invention is further illustrated by the following non-limitative examples.

EXAMPLE 1

A composition for a glossy iodine-resistant coating was made, containing:
28.4 g of demi-water
2.8 g of itaconic acid (methylenesuccinic acid) (ex Merck)
9.0 g of ethyl alcohol
29.3 g of tetraethoxysilane (TEOS)
20.4 g of glycidoxypropyl trimethoxysilane (GLYMO)
72.8 g of silica dispersion (Ludox® TMA; ex Aldrich)
1.1 g of wetting agent (Tegowet® 280; ex Tego Chemie)

14.2 g of demi-water was brought into a beaker and 9.1 g of Ludox® TMA were added and the mixture was stirred for 2 hours or until a nice dispersion without clogged particles was formed. The beaker was closed and this pre-mix was put aside.

In another beaker, 14.2 g of demi-water, 9.0 g of ethyl alcohol and 2.8 g of itaconic acid were added and stirred until the acid was completely dissolved.

Under stirring 29.3 g of TEOS were added followed by 20.4 g of GLYMO and the mixture was stirring for 45 minutes.

After 45 minutes the pre-mix was added slowly under stirring and stirring was maintained for 5 minutes. Thereafter 1.1. g of Tegowet 280 were added slowly under stirring and stirring was maintained for 5 minutes. After 5 minutes the beaker with the mixture was closed, and very slowly stirred or just put aside for at least 24 hours to bring the hydrolization reaction to completion, after which the mixture was ready for use for application by spraying, dipping, dispensing, or any other application methods for wet compositions.

The pot-life of the mixture was at least 3 days.

EXAMPLE 2

A composition for a matted iodine-resistant coating was made, containing:
28.4 g of demi-water
g of itaconic acid (methylenesuccinic acid)(ex Merck)
g of ethyl alcohol
29.3 g of tetraethoxysilane (TEOS)
20.4 g of glycidoxypropyl trimethoxysilane (GLYMO)
72.8 g of silica dispersion (Ludox® TMA; ex Aldrich)
3.0 g of matting agent (Syloid® ED 30; ex Grace)
1.1 g of wetting agent (Tegowet® 280; ex Tego Chemie)

The composition was made according to Example 1, with Syloid ED 30 added slowly step by step to the Ludox® TMA/demi-water mixture while stirring (3.0 g in total) and stirring was maintained for 2 hours or until a nice dispersion without clogged particles was formed.

EXAMPLE 3

Surface contact-test
Procedure:
A tissue, which was free from wood fiber, was soaked into a 70 wt. % iodine solution in ethyl alcohol and was put onto a surface for testing, which was coated with various coating (see Table). The soaked tissue was shielded mainly from the open air by placing a plastic beaker with a small hole (diameter about 1-2 mm) in the bottom thereof upside down over the tissue.

The maximum contact time in hours for which discoloration did not occur, was determined by visual inspection. A contact time of at least 24 h is required to be classified as sufficiently iodine staining proof.

Results with Different Coating Types

TABLE

| Entry | Coating type | Contact time in h |
|---|---|---|
| 1 | two-component poly-urethane solvent borne, curing at 80° C., Dualux ™/VM01, ex: Akzo Nobel (Sassenheim, NL) | <1 |
| 2 | two-component poly-urethane waterborne, curing at 80° C., Formulation M-400, ex: Neoresins (Waalwijk, NL) | <1 |
| 3 | two-component epoxide, curing at 80° C., Sigma CM/CM, ex: Sigma Coatings (Uithoorn, NL) | <1 |
| 4 | special purpose epoxy polysiloxane hybrid, anti graffiti coating, curing at 20° C., PSX 700/Amercoat 4093, ex: Ameron Int. (Geldermalsen, NL) | <1 |
| 5 | sol-gel hybrid, silica type, curing at 80° C., MP-100, ex SDC Coatings (GB) | >3 |
| 6 | sol-gel hybrid, silica type, UV curing at 20° C., Desolite 4D5-15, ex DSM Desotech (USA) | >3 |
| 7 | sol-gel hybrid, silica type, curing at 80° C. (composition of Example 1) | >3 |
| 8 | sol-gel hybrid, silica type, curing at 80° C. (composition of Example 2) | >3 |

The invention claimed is:

1. A medical apparatus comprising at least one surface which is at least partially coated with a hydrolytically condensed organosilane sol-gel composition, wherein the organosilane sol-gel composition comprises a mixture of tetraethoxysilane, methyltrimethoxysilane, and organosilane compounds that contain an organic, polymerizable substituent, wherein the organosilane compounds that contain the organic, polymerizable substituent consist of 3-glycidoxypropyl trimethoxysilane, methacryloxypropyl trimethoxysilane and vinyl trimethoxysilane, and wherein the organosilane sol-gel composition is further formed from dimethylmalonic acid.

2. The medical apparatus according to claim 1, wherein the sol-gel composition further comprises a material formed from a mixture of an organosilane compound and silica particles.

3. The medical apparatus according to claim 1, wherein the coating can be cured at a curing temperature of about 80° or lower, wherein responsive to being cured, the coating exhibits resistance to iodine staining and cracking.

4. The medical apparatus of claim 1, wherein said surface is a tabletop of a diagnostic system.

5. A process for making medical equipment resistant to iodine comprising coating one or more surfaces with a hydrolytically condensed organosilane sol-gel composition, wherein the organosilane sol-gel composition comprises a mixture of tetraethoxysilane, methyltrimethoxysilane, and organosilane compounds that contain an organic, polymerizable substituent, wherein the organosilane compounds that contain the organic, polymerizable substituent consist of 3-glycidoxypropyl trimethoxysilane, methacryloxypropyl trimethoxysilane and vinyl trimethoxysilane, and wherein the organosilane sol-gel composition is further formed from dimethylmalonic acid.

6. The process of claim 5 wherein said sol-gel composition is a glossy material, and further comprises silica particles.

7. The process of claim 5 wherein said sol-gel composition is a matte material, and further comprises particles and a matting agent.

* * * * *